United States Patent [19]

Hartley et al.

[11] 4,278,673

[45] Jul. 14, 1981

[54] PHARMACOLOGICALLY ACTIVE COMPOUNDS

[75] Inventors: David Hartley, Ware; Alexander W. Oxford, Royston, both of England

[73] Assignee: Allen & Hanburys Limited, London, England

[21] Appl. No.: 72,098

[22] Filed: Sep. 4, 1979

Related U.S. Application Data

[63] Continuation of Ser. No. 888,522, Mar. 21, 1979, abandoned.

[30] Foreign Application Priority Data

Mar. 25, 1977 [GB] United Kingdom ............... 12598/77
Nov. 14, 1977 [GB] United Kingdom ............... 47250/77

[51] Int. Cl.³ ................ C07D 487/04; A61K 31/415
[52] U.S. Cl. ..................................... 424/249; 544/184
[58] Field of Search ......................... 544/184; 424/249

[56] References Cited

U.S. PATENT DOCUMENTS 3,941,785  3/1976  Clarke et al. ........................ 544/184

FOREIGN PATENT DOCUMENTS 1400999  7/1975  United Kingdom .................... 544/184

Primary Examiner—John M. Ford
Attorney, Agent, or Firm—Bacon & Thomas

[57] ABSTRACT

There are provided compounds of the general formula (I):

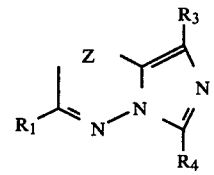

and physiologically acceptable salts thereof in which Z represents a group

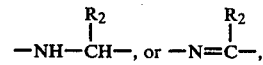

wherein $R_2$ represents a hydrogen atom or a straight or branched chain alkyl radical, or Z can additionally represent a group

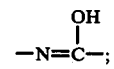

and $R_1$, $R_3$ and $R_4$, which may be the same or different, each represent a hydrogen atom, a cycloalkyl group, an aryl group which may optionally be substituted by one or more hydroxy, alkoxy, or halogen radicals, or a straight or branched alkyl or alkenyl group, which alkyl or alkenyl group may be substituted with an aryl group, which aryl group may optionally be substituted by one or more hydroxy, alkoxy or halogen radicals. The compounds possess spasmolytic and cAMP phosphodiesterase inhibitory activity.

14 Claims, No Drawings

PHARMACOLOGICALLY ACTIVE COMPOUNDS

This is a continuation, of application Ser. No. 888,522, filed Mar. 21, 1978, now abandoned.

This invention relates to certain heterocyclic compounds having pharmacological activity, and to processes for the preparation thereof, as well as to pharmaceutical compositions containing them, and their use in medical treatment.

We have found that certain imidazo [5,1-f]-1,2,4-triazines and derivatives thereof possess spasmolytic and cyclic adenosine monophosphate (cAMP) phosphodiesterase inhibitory activity. They are therefore particularly useful as bronchodilators in the treatment of diseases involving constriction of bronchial muscle, for example, asthma and bronchitis. The compounds may also be useful for the treatment of pulmonary oedema and congestive heart failure, and for topical application as in the treatment of skin disorders, for example psoriasis.

The present invention therefore provides compounds of the general formula I:

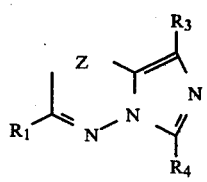

and physiologically acceptable salts thereof in which Z represents a group

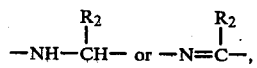

wherein $R_2$ represents a hydrogen atom or a straight or branched chain alkyl radical, or Z can additionally represent a group

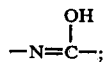

and $R_1$, $R_3$ and $R_4$, which may be the same or different, each represent a hydrogen atom, a cycloalkyl group, an aryl group which may optionally be substituted by one or more hydroxy, alkoxy or halogen radicals, or a straight or branched alkyl or alkenyl group, which alkyl or alkenyl group may be substituted with an aryl group, which aryl group may in turn optionally be substituted by one or more hydroxy, alkoxy or halogen radicals. When Z represents the group

the compound may exist in its tautomeric form as a lactam (II) and such tautomeric forms are within the scope of the invention

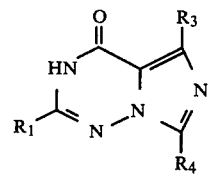

The term alkyl preferably refers to a group containing 1 to 6 carbon atoms, in particular 1 to 4 carbon atoms; and the term alkenyl a group containing 2 to 6, in particular 3 to 5 carbon atoms. The term aryl preferably indicates phenyl. Cycloalkyl preferably means a group which contains 3 to 7 carbon atoms. The term alkoxy preferably refers to a group containing 1 to 4 carbon atoms and the term halogen radicals preferably refers to fluorine or chlorine groups.

Particularly preferred meanings for the groups $R_1$–$R_4$ are as follows:

$R_1$ is hydrogen; alkyl, preferably methyl, ethyl or isopropyl; aryl, preferably phenyl; or aralkyl, preferably benzyl or phenethyl;

$R_2$ is hydrogen or alkyl, preferably methyl;

$R_3$ is alkyl, preferably methyl; or aryl, preferably phenyl; and $R_4$ is alkyl, preferably methyl, propyl or isobutyl; or cycloalkyl, preferably cyclopentyl.

Particularly preferred compounds are:
2,5-dimethyl-7-(2-methylpropyl)imidazo[5,1-f]-1,2,4-triazin-4(3H)-one, 3,4-dihydro-2,5-dimethyl-7-propylimidazo[5,1-f]-1,2,4-triazine and 3,4-dihydro-7-(2-methylpropyl)-2,4,5-trimethylimidazo[5,1-f]-1,2,4-triazine, and physiologically acceptable salts thereof.

The spasmolytic activity of the compounds of the invention was demonstrated by their abilities in the isolated guinea-pig tracheal strip preparation to relax spontaneous tone and to reverse the spasmogenic action of methacholine (R. F. Coburn and T. Tomita. Am. J. Physiol., 1973, 224, 1072–1080). In the anaesthetised guinea-pig the compounds reduce intratracheal pressure (G. W. Lynn-James, J. Pharm. Pharmac., 1969, 21, 379–386).

The ability of compounds according to the invention to inhibit the cAMP phosphodiesterase was demonstrated on an enzyme preparation from human lung on the basis of the method described by T. R. Russell, W. L. Terasaki and M. M. Appleman (1973) J. Biol. Chem. 248, 1334–1340.

In addition compounds in which Z is

have the advantage that they selectively reduce intratracheal pressure without increasing heart rate in the anaesthetised guinea-pig. They also exhibit an interesting profile of action in that at low concentrations they cause a spasmolytic effect resulting from enhanced intracellular levels of cAMP but this effect is due neither to stimulation of β-andrenoceptors nor to inhibition of cAMP phosphodiesterase. Inhibition of cAMP phosphodiesterase occurs at much higher concentrations than those required to cause a spasmolytic action. Thus, the ratio of spasmolytic activity to cAMP phosphodiesterase inhibitory activity is high.

Intracellular levels of cAMP were measured on the basis of the procedure described by B. L. Brown, J. D. M. Albano, R. P. Ekins and A. M. Scherzi (Biochem. J. 1971, 121, 561–2).

The compounds according to the invention may conveniently be prepared by methods analogous to those described in U.K. Patent Specification Nos. 1,400,999 and 1,457,873.

Thus a compound of the invention as represented by formula II may be prepared by treating a compound of formula III, wherein $R_1$, $R_3$ and $R_4$ have the meanings given above, with a suitable cyclodehydrating agent capable of concomitant N-debenzylation under the conditions of the reaction, such as phosphorus oxychloride, optionally in the presence of a solvent such as a halogenated hydrocarbon, for example dichloroethane. Alternatively the compound III may be converted into compound IV by removal of the benzyl group by for example hydrogenolysis in the presence of a noble metal catalyst. The reaction of IV with a suitable cyclodehydrating reagent such as polyphosphoric acid or phosphorus oxychloride or polyphosphoric ester then gives the required compound II. Again this reaction may optionally be carried out in the presence of a solvent, for example dichloroethane.

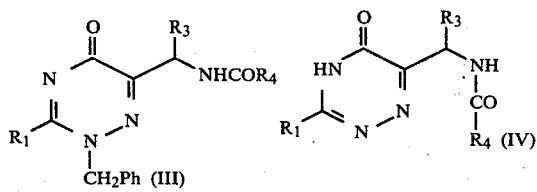

In addition to the routes described in U.K. Patent Specification No. 1,400,999 the compound IV may be prepared by the novel route which is described below with reference to the reaction scheme given.

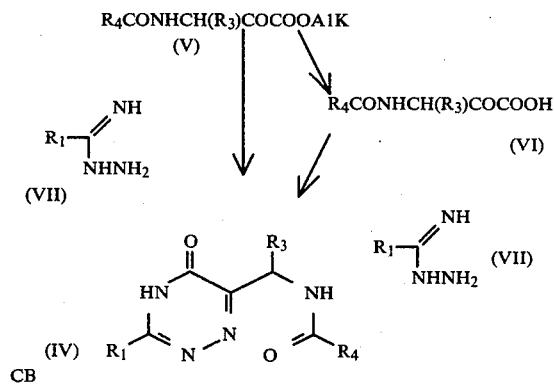

In this process an α-ketoester (V) is subjected to reaction with an appropriate amidrazone (VII) in a suitable solvent such as ethanol. The amidrazone (VII) is conveniently generated in situ by treatment of the corresponding amidine hydrochloride with hydrazine. Alternatively the triazinone (IV) may be prepared by treatment of the α-ketoester (V) with an appropriate amidrazone hydroiodide, again suitably in a solvent such as ethanol. In a further alternative process the α-ketoester may first be converted into the corresponding keto acid (VI) which is then transformed into the triazinone (IV). This novel route has the advantage that it involves less steps than the previously described routes.

The keto ester (V) may be prepared from an N-acylamino acid of the formula $R_4CONHCH(R_3)COOH$. This is reacted with a suitable acid chloride conveniently an alkyl oxalyl chloride in the presence of a suitable base such as pyridine, 4-dimethylaminopyridine or picoline, according to the conditions of the Dakin-West reaction but with isolation of the intermediate isomeric enol esters of the formulae (VIII) and (IX):

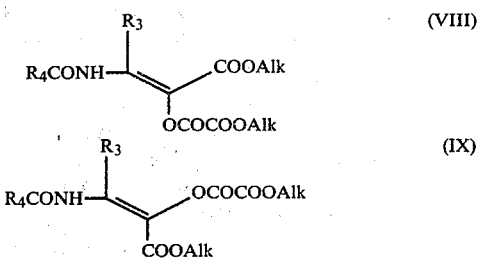

These esters may then be hydrolysed, for example, with a mild acid or base to the α-ketoester of formula (V).

The compounds of the invention as represented by formula (X) below, in which $R_2$ represents a hydrogen atom may be prepared by reduction of the compounds of formula (II). Suitable reducing agents include diborane or complex metal hydrides such as lithium aluminium hydride and sodium dihydro-bis(2-methoxyethoxy) aluminate. The reaction is carried out in an aprotic solvent, for example tetrahydrofuran, ether, dimethoxyethane or diglyme, and if desired with heating.

The compounds of the invention, as represented by formula (XI) below, in which $R_2$ represents a hydrogen atom may be prepared by dehydrogenation of the compound (X) in which $R_2$ represents hydrogen. The dehydrogenation may be carried out using an oxidising agent for example potassium ferricyanide or by heating with palladium oxide on charcoal in an inert solvent, preferably a high boiling inert solvent such as p-cymene or decalin.

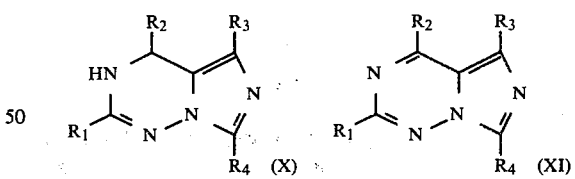

Compounds of formula (X) in which $R_2$ represents an alkyl group may conveniently be prepared by reacting a compound of formula (XI) in which $R_2$ represents hydrogen with a metal alkyl such as a lithium alkyl or a Grignard reagent, conveniently in a solvent such as diethyl ether or tetrahydrofuran. Dehydrogenation of the compounds (X) in which $R_2$ represents alkyl using the conditions referred to above gives the corresponding compound (XI) in which $R_2$ represents alkyl.

The compounds according to the invention may be formulated for use in human and veterinary medicine for therapeutic and prophylactic purposes. They may be used in the form of their physiologically acceptable salts, in particular acid addition salts, if desired. Preferred salts include the hydrochloride, sulphate, maleate, tartrate etc. Such compounds may be presented for use in the conventional manner with the aid of carriers or excipients and formulating agents as required, and with or without supplementary medicinal agents. The compositions may include solid and liquid preparations for oral use, suppositories or injections, or forms suitable for administration by inhalation. Convenient oral presentations are in the form of tablets. Injections may be formulated with the aid of physiologically acceptable carriers and agents as solutions, suspensions or as dry products for reconstitution before use. For administration by inhalation the compounds according to the invention are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount. A typical dose for treating asthma in humans is from 1–1200 mg. depending on the age, weight and condition of the patient and the route of administration.

The compounds according to the invention may be formulated in combination with compounds that have stimulant activity at the β-adrenoreceptors such as a salbutamol, isoprenaline, clenbuterol, procaterol and terbutaline etc. The provision of therapeutic compositions comprising as active ingredients, a compound according to the invention and a β-adrenoreceptor stimulant, in particular salbutamol, represents an important aspect of the invention.

The following Examples illustrate the invention. Examples 1, 2 and 3 describe the production of intermediates and illustrate the novel route herein referred to.

EXAMPLE 1

(i) Ethyl-3-isovaleramido-2-oxo-butyrate

Ethyl oxalyl chloride (212 g) was added dropwise with stirring to a solution of isovalerylalanine (136 g) and pyridine (186.5 g) in anhydrous tetrahydrofuran (500 ml) at a rate sufficient to initiate refluxing. The reaction mixture was stirred and heated at reflux for 5 hours. The cooled reaction mixture was treated with water (1000 ml) and extracted with ethyl acetate (4×400 ml). The combined organic extracts were washed with water (3×200 ml) and dried (anhydrous sodium sulphate). Removal of solvent provided a yellow syrup which was evaporated with benzene (2×200 ml) to yield the isomeric enol esters of the title compound.

These were dissolved in absolute ethanol (400 ml) and heated at reflux in the presence of sodium bicarbonate (70 g) for 3 hours. After cooling, the sodium bicarbonate was filtered off and the filtrate was evaporated in vacuo. The resultant residue was taken up in ethyl acetate (500 ml) and washed with water (4×100 ml). The dried (anhydrous sodium sulphate) ethyl acetate phase was evaporated in vacuo to provide crude α-ketoester as a golden syrup, 147 g.

(ii) In a similar manner was prepared ethyl-3-cyclopentanecarboxamido-2-oxobutyrate as an oil from N-(cyclopentylcarbonyl)-alanine (5.55 g), the oil was used directly in the next stage.

(iii) In a similar manner was prepared ethyl 3-butyramido-2-oxo-3-phenylpropionate (7.6 g) as an oil, from butyryl α-phenylglycine (22.1 g).

EXAMPLE 2

(i) 6-(1-Isovaleramidoethyl)-3-(1-methylethyl)-1,2,4-triazin-5(4H)-one

Isobutyrylamidine hydrochloride (4.5 g) was dissolved in absolute ethanol (25 ml) and the solution cooled in ice. Hydrazine hydrate (1.84 g) in absolute ethanol (5 ml) was added dropwise (25 min) with stirring. After completion of the addition stirring was continued at room temperature for 10 minutes. A solution of ethyl-3-isovaleramido-2-oxobutyrate (8.45 g) in absolute ethanol (20 ml) was added and the mixture heated at 50°–60° C. for 26 hours. The reaction mixture was concentrated in vacuo, triturated with ethyl acetate and the resultant crystalline triazinone collected by filtration, washed thoroughly with water and dried. The ethyl acetate solution was concentrated and applied to a column of silica gel. Elution with ethyl acetate containing 2–5% ethanol provided a further quantity of the triazinone. The product was recrystallised from ethyl acetate, 1.72 g, m.p. 203°–205°.

(ii) In a similar manner was prepared 3-benzyl-6-(1-isovaleramidoethyl)-1,2,4-triazin-5(4H)-one, 10 g, m.p. 190°–193° (from ethanol-ethyl acetate) from phenylacetamidine hydrochloride (29.5 g) and ethyl 3-isovaleramido-2-oxobutyrate (42.1 g).

(iii) In a similar manner was prepared 6-(1-cyclopentanecarboxamidoethyl)-3-methyl-1,2,4-triazin-5(4H)-one, 1.02 g, m.p. 211°–214° (from ethyl acetate) from acetamidine hydrochloride (1.89 g) and ethyl 3-cyclopentanecarboxamido-2-oxobutyrate.

(iv) In a similar manner was prepared 6-(1-isovaleramidoethyl)-1,2,4-triazin-5(4H)-one (12.0 g) [the hydrochloride had m.p. 167°–169° (from ethanol-ethyl acetate)], from formamidine acetate (41.75 g) and ethyl 3-isovaleramido-2-oxobutyrate (127.4 g).

(v) In a similar manner was prepared 6-(1-butyramidoethyl)-3-ethyl-1,2,4-triazin-5(4H)-one, 15.4 g, m.p. 174°–177° (from ethanol) from propionamidine hydrochloride (48.8 g) and ethyl 3-butyramido-2-oxobutyrate (96.8 g).

(vi) In a similar manner was prepared 3-benzyl-6-(1-butyramidoethyl)-1,2,4-triazin-5(4H)-one, 7.81 g, m.p. 175.5°–177° (from ethanol) from phenacetamidine hydrochloride (40.26 g) and ethyl 3-butyramido-2-oxobutyrate (69.5 g).

(vii) In a similar manner was prepared 6-(1-butyramidoethyl)-3-(2-phenylethyl)-1,2,4-triazin-5(4H)-one, 5.56 g, m.p. 201°–201.5° (from ethanol) from 3-phenylpropionamidine hydrochloride (12.27 g) and ethyl 3-butyramido-2-oxobutyrate (25 g).

(viii) In a similar manner was prepared 6-butyramidobenzyl-3-methyl-1,2,4-triazin-5(4H)-one (1.36 g), m.p. 210°–212° (from ethyl acetate), from acetamidine hydrochloride (2.66 g) and ethyl 3-butyramido-2-oxo-3-phenylpropionate (7.8 g).

EXAMPLE 3

(i) 6-(1-Butyramidoethyl)-3-methyl-1,2,4-triazin-5(4H)-one

Acetamidrazone hydroiodide (6.63 g) was heated with ethyl 3-butyramido-2-oxobutyrate (7.01 g) in absolute ethanol (40 ml) at 80° for 50 minutes. The dark red solution was concentrated to a viscous oil which was triturated with ethyl acetate to give the triazinone as a yellow solid (1.65 g). The filtrate was concentrated and chromatographed on silica gel. Fractions eluted with ethyl acetate-ethanol (4:1) afforded a second crop (0.31 g). The two crops were combined and recrystallised from ethanol to give material, m.p. 235°–237.5°, 1.69 g.

(ii) In a similar manner was prepared 6-(1-isovaleramidoethyl)-3-phenyl-1,2,4-triazin-5(4H)-one, 6.2 g, m.p. 236°–238°, from benzamidrazone hydroiodide (26.4 g) and ethyl 3-isovaleramido-2-oxobutyrate (22.9 g).

EXAMPLE 4

(i) 2-(1-Methylethyl)-5-methyl-7-(2-methylpropyl)imidazo [5,1-f]-1,2,4-triazin-4(3H)-one, hydrochloride 6-(1-Isovaleramidoethyl)-3-(1-methylethyl)-1,2,4-triazin-5(4H)-one (1.55 g) was added with stirring to polyphosphoric acid (15 g) at 150°. After complete dissolution of the added triazinone derivative the reaction mixture was maintained at 150° with occasional stirring for 1 hour. The cooled reaction mixture was then added to ice-water and the solution adjusted to pH 7.5 by addition of 8% aqueous sodium bicarbonate solution. The precipitated product was collected by filtration and recrystallised from ether to give 0.81 g of the product, m.p. 135°–137°. This was converted into a hydrochloride salt, m.p. 208°–211° (from ethanol-ethyl acetate).

(ii) In a similar manner was prepared 5-methyl-2-phenyl-7-(2-methylpropyl)imidazo[5,1-f]-1,2,4-triazin-4(3H)-one, 0.4 g, m.p. 253°–255° (from ethyl acetate) from 6-(1-isovaleramido)-ethyl-3-phenyl-1,2,4-triazin-5(4H)-one (0.7 g).

(iii) In a similar manner was prepared 2-methyl-5-phenyl-7-propylimidazo[5,1-f]-1,2,4-triazin-4(3H)-one (0.26 g) m.p. 190°–191° (from ethyl acetate) from 6-butyramidobenzyl-3-methyl-1,2,4-triazin-5(4H)-one (0.70 g).

(iv) In a similar manner was prepared 2-benzyl-5-methyl-7-(2-methylpropyl)imidazo[5,1-f]-1,2,4-triazin-4(3H)-one (1.26 g), m.p. 164°–165° (from ethyl acetate) (the hydrochloride had m.p. 236.5°–240° from ethanol-ethyl acetate), from 3-benzyl-6-(1-isovaleramidoethyl)-1,2,4-triazin-5(4H)-one (2.0 g).

(v) In a similar manner was prepared 7-cyclopentyl-2,5-dimethylimidazo[5,1-f]triazin-4(3H)-one, 0.4 g, m.p. 208°–210° (from ethyl acetate) (the hydrochloride salt had m.p. 272°–274°, from ethanol), from 6-(1-cyclopentanecarboxamidoethyl)-3-methyltriazin-5(4H)-one (0.7 g).

(vi) In a similar manner was prepared 5-methyl-7-(2-methylpropyl)imidazo[5,1-f]-1,2,4-triazin-4(3H)-one, 0.12 g, m.p. 227°–229° (from ether), (the hydrochloride salt had m.p. 184°–186° from ethanol-ethyl acetate) from 6-(1-isovaleramidoethyl)-1,2,4-triazin-5(4H)-one (0.4 g).

(vii) In a similar manner was prepared 2-ethyl-5-methyl-7-propylimidazo[5,1-f]-1,2,4-triazin-4(3H)-one, 4.6 g, m.p. 215°–217° (from ethyl acetate) (the hydrochloride had m.p. 212°–213°, from ethanol-ethyl acetate) from 6-(1-butyramidoethyl)-3-ethyl-1,2,4-triazin-5(4H)-one (11.9 g).

(vii) In a similar manner was prepared 2-benzyl-5-methyl-7-propylimidazo[5,1-f]-1,2,4-triazin-4(3H)-one, 5.14 g, m.p. 156°–157° (from ethyl acetate) (the hydrochloride salt had m.p. 247.5°–249.5° from ethanol-ethyl acetate), from 2-benzyl-6-(1-butyramidoethyl)-1,2,4-triazin-5(4H)-one (6.45 g).

(ix) In a similar manner was prepared 2-(2-phenylethyl)-5-methyl-7-propylimidazo[5,1-f]-1,2,4-triazin-4(3H)-one, 8.78 g, m.p. 156°–159.5° (from ethyl acetate) (the hydrochloride salt had m.p. 198.5°–200.5° from ethanol-ethyl acetate) from 6-(1-butyramidoethyl)-3-(2-phenylethyl)-1,2,4-triazin-5(4H)-one (13.22 g).

EXAMPLE 5

2,5-Dimethyl-7-isobutylimidazo[5,1-f]-1,2,4-triazin-4(3H)-one (a) 6-(1-Isovaleramidoethyl)-3-methyl-1,2,4-triazin-5(4H)-one Hydrazine hydrate (100%, 78 ml, 80 g) in absolute ethanol (40 ml) was added with stirring over a period of 15 minutes to a solution of acetamidine hydrochloride (151 g) in absolute ethanol (1200 ml) cooled to 5°. The mixture was stirred for a further 10 minutes, then ethyl-3-isovaleramido-2-oxobutyrate [prepared by hydrolysis of the enol esters (535 g) as in Example 1(i)] in absolute ethanol (200 ml) was added and heated at 70°–80° with stirring for 20 hours. After cooling the mixture to room temperature, ammonium chloride was removed by filtration and the filtrate concentrated and diluted with ethyl acetate (250 ml) to precipitate the triazinone (94.0 g). The filtrate on standing deposited a second crop (6.7 g). Two recrystallisations from ethanol gave a sample of m.p. 224°–226°.

(b) 2,5-Dimethyl-7-isobutylimidazo[5,1-f]-1,2,4-triazin-4(3H)-one 6-(1-Isovaleramidoethyl)-3-methyl-1,2,4-triazin-5(4H)-one (91.6 g) was added portionwise with stirring to polyphosphoric acid (800 g), heated to 150°. All the solid dissolved in about 15 minutes, and the mixture was then cooled to 100° and poured onto ice water (3 liters). The solution was brought to pH 7 by addition of sodium carbonate and the imidazotriazinone precipitated and was collected. The filtrate was extracted with ethyl acetate (3 liters) to give a second crop which was combined with the first and recrystallised from ethyl acetate to give white needles m.p. 186°–188°, 53.1 g.

The hydrochloride salt had m.p. 227°–229° from ethyl acetate-ethanol.

EXAMPLE 6

2,5-Dimethyl-7-propylimidazo[5,1-f]-1,2,4-triazin-4(3H)-one

A mixture of 6-(1-butyramido)ethyl-3-methyl-1,2,4-triazin-5(4H)-one (1.47 g) and phosphorus oxychloride (5 ml) in 1,2-dichloroethane (40 ml) was heated under reflux for 2 hours. The solvent was removed in vacuo and to the residue was added 2 N sodium carbonate (50 ml) and ethyl acetate (30 ml) and the mixture vigorously stirred until all the solid dissolved. The organic layer was separated and the aqueous solution extracted further with ethyl acetate (2×50 ml). The extracts were then combined and dried. Removal of the solvent gave the imidazotriazinone as an off-white solid (1.30 g). Recrystallisation from ethyl acetate gave a sample m.p. 229.5°–234°, 1.03 g.

EXAMPLE 7

(i) 2,5,7-Trimethylimidazo[5,1-f]-1,2,4-triazin-4(3H)-one (a) 2,5-Dihydro-3,α-dimethyl-5-oxo-1,2,4-triazine-6-acetic acid, ethyl ester Hydrazine hydrate (100%, 78 ml) was added dropwise with stirring to a solution of acetamidine hydrochloride (151 g) in absolute ethanol (1.2 liters) keeping the temperature at 0° to −2°. The addition was complete after 15 minutes. The mixture was stirred for a further 15 minutes and then the cooling bath was removed. Diethyl oxalopropionate (322.5 g) was added and the temperature rose to 30°. The mixture was heated at this temperature for 30 minutes, then at 80° for 5½ hours. The dark yellow solution was cooled, filtered to remove ammonium chloride and concentrated to an oil. This was taken up into cold water (1 liter) and the yellow solid that separated was removed by filtration and discarded. The filtrate was extracted with cyclohexane to remove unchanged diethyl oxalopropionate and then with ethyl acetate (7×200 ml) and continuously for 46 hours to give an oil which on trituration with ether gave the triazinone as a pale yellow solid, 118.4 g, m.p. 127.5°–129° (from ethyl acetate-cyclohexane).

(b) 2-Benzyl-2,5-dihydro-3,α-dimethyl-1,5-oxo-1,2,4-triazine-6-acetic acid, ethyl ester Benzyl chloride (4.0 g), sodium iodide (4.73 g), 2,5-dihydro-3,α-dimethyl-5-oxo-1,2,4-triazine-6-acetic acid, ethyl ester (6.3 g) and finely powdered anhydrous potassium carbonate (4.34 g) were stirred together in ethyl methyl ketone (300 ml) heated under reflux for 2½ hours. The solution was filtered to remove inorganic material and concentrated to an oil. This was taken up into ethyl acetate (400 ml) and the solution was washed with water (2×100 ml) and dried. Removal of the solvent gave an oil which solidified on trituration with ether and cyclohexane. Recrystallisation from ethyl acetate-ether gave the benzylated triazinone as prisms, 4.74 g, m.p. 94.5°–98°.

(c) 2-Benzyl-2,5-dihydro-3,α-dimethyl-5-oxo-1,2,4-triazine-6-acetic acid, hydrazide 2-Benzyl-2,5-dihydro-3,α-dimethyl-5-oxo-1,2,4-triazine-6-acetic acid, ethyl ester (60.0 g) was taken up in methanol (600 ml) and the solution, chilled in ice, was treated with hydrazine hydrate (200 ml) added dropwise with stirring over a period of 10 minutes. The solution was kept at room temperature for 16 hours and then concentrated to a yellow crystalline mass. Azeotropic distillation with toluene removed residual traces of hydrazine. Recrystallisation from isopropanol afforded the hydrazide as needles, 19.79 g, m.p. 171°–174°.

(d) 6-(1-Aminomethyl)-2-benzyl-3-methyl-1,2,4-triazin-5(4H)-one

Sodium nitrite (1.29 g) in water (25 ml) was added to a stirred solution of 2-benzyl-2,5-dihydro-3,α-dimethyl-5-oxo-1,2,4-triazine-6-acetic acid, hydrazide (5.0 g) in conc. hydrochloric acid (3.3 ml) and water (75 ml) keeping the temperature at −1° to −2°. The azide separated as a white solid which rapidly became a thick gum. Conc. hydrochloric acid (5 ml) was added and the mixture was raised to 65° over 30 minutes and left at this temperature for 2 hours. During this period the gum gradually dissolved to give a clear yellow solution. This was cooled and brought to pH 8 by the addition of sodium bicarbonate. Water was removed by rotary evaporation and the residual solid was extracted with boiling isopropanol (6×100 ml). The extract was filtered and concentrated to give the amine as a gum (4.37 g) which failed to crystallise.

(e) (i) 6-(1-Acetamidoethyl)-2-benzyl-3-methyl-1,2,4-triazin-5(4H)-one

Dry dioxan (80 ml) was added to 6-(1-aminomethyl)-2-benzyl-3-methyl-1,2,4-triazin-5(4H)-one (4.34 g) and the cloudy suspension stirred at room temperature was treated with acetic anhydride (1.9 ml). The mixture was stirred for 2 hours then concentrated to a brown solid. Recrystallisation from ethanol-ether afforded the acetamide, 3.1 g, m.p. 196°–203°.

(ii) In a similar manner was prepared 2-benzyl-6-(1-butyramidoethyl)-3-methyl-1,2,4-triazin-5(4H)-one, 6.55 g, m.p. 168°–169° (from ethyl acetate) by acylation of 6-(1-aminomethyl)-2-benzyl-3-methyl-1,2,4-triazin-5(4H)-one (8.66 g) with butyric anhydride.

(f) (i) 2,5,7-Trimethylimidazo[5,1-f]-1,2,4-triazin-4(3H)-one

Phosphorus oxychloride (5 ml) was added to a cloudy solution of 6-(1-acetamidoethyl)-2-benzyl-3-methyl-1,2,4-triazin-5(4H)-one (1.5 g) in 1,2-dichloroethane (25 ml). There was a slight exothermic reaction, the solution darkened and a dark yellow gum separated. The mixture was heated to boiling over 10 minutes then refluxed for 10 minutes. During this period the gum dissolved to give a dark yellow solution which was cooled and poured onto ice water (50 ml). The aqueous layer was basified with sodium bicarbonate and the mixture was extracted with ethyl acetate (2×100 ml, 8×50 ml). The extracts were dried and removal of the solvent gave the imidazotriazinone as a buff solid, 0.57 g, m.p. 322°–323° (from ethanol).

(ii) In a similar manner was prepared 2,5-dimethyl-7-propylimidazo[5,1-f]-1,2,4-triazin-4(3H)-one, 0.43 g, m.p. 232°–236° (from ethyl acetate) from 2-benzyl-6-(1-butyramidoethyl)-3-methyl-1,2,4-triazin-5(4H)-one (1.5 g).

EXAMPLE 8

(i) 3,4-Dihydro-2,5-dimethyl-7-isobutylimidazo[5,1-f]-1,2,4-triazine, maleate

Lithium aluminium hydride (2.3 g) was added importions with stirring to anhydrous tetrahydrofuran (200 ml) under nitrogen. A solution of 2,5-dimethyl-7-isobutylimidazo-[5,1-f]-1,2,4-triazin-4(3H)-one (5.0 g) in anhydrous tetrahydrofuran (150 ml) was added dropwise and the mixture stirred and heated gently under reflux for 16 hours.

After cooling to room temperature the excess of lithium aluminium hydride was destroyed by the sequential addition of water (2.3 ml), 15% sodium hydroxide solution (2.3 ml) and finally water (6.9 ml).

The resultant suspension was filtered through a diatomaceous earth and the filtrate concentrated under reduced pressure to an oil which crystallised on standing. The white crystals were filtered, recrystallised from ethyl acetate and dried in vacuo to give 3.9 g, m.p. 165°–168°.

This base was dissolved in a mixture of dry ether/ethyl acetate/trace ethanol (ca. 50 ml total volume) and added to a warm solution of maleic acid (1.2 g) in dry ether/ethyl acetate (50 ml). The suspension formed was concentrated to ca. 70 ml and cooled to room temperature. The white crystals were filtered off and recrystallised from isopropanol/dry ether to give 2.0 g, m.p. 145°–148°.

(ii) In a similar manner was prepared 3,4-dihydro-5-methyl-7-(2-methylpropyl)imidazo[5,1-f]-1,2,4-triazine, 0.22 g, m.p. 146.5°–149° (from ether) from 5-methyl-7-(2-methylpropyl) imidazo[5,1-f]triazin-4(3H)-one (1.3 g) in 1,2-dimethoxyethane.

(iii) In a similar manner was prepared 3,4-dihydro-2-ethyl-5-methyl-7-propylimidazo[5,1-f]-1,2,4-triazine, 1.03 g, m.p. 115°–117° (from ethyl acetate) (the hydrochloride salt had m.p. 234°–235° from ethanol-ethyl acetate)from 2-ethyl-5-methyl-7-propylimidazo[5,1-f]-1,2,4-triazin-4(3H)-one (3.49 g) in 1,2-dimethoxyethane.

(iv) In a similar manner was prepared 3,4-dihydro-5-methyl-2-(2-phenylethyl)-7-propylimidazo[5,1-f]-1,2,4- triazine, 1.81 g, m.p. 115°–116.5° (from ether) (the hydrochloric salt had m.p. 171°–171.5° from ethanol-ethyl acetate) from 5-methyl-2-(2-phenylethyl)-7-propylimidazo[5,1-f]-1,2,4-triazin-4(3H)-one (2.0 g) in 1,2-dimethoxyethane.

(v) In a similar manner was prepared 3,4-dihydro-2,5,7-trimethylimidazo[5,1-f]-1,2,4-triazine, 0.89 g, m.p. 250°–252° (from ethyl acetate) (the maleate salt had m.p. 178°–180° from ethanol-ethyl acetate) from 2,5,7-trimethylimidazo[5,1-f]-1,2,4-triazin-4(3H)-one (1.07 g) in 1,2-dimethoxyethane.

EXAMPLE 9

(i) 2,5-Dimethyl-7-(2-methylpropyl)imidazo[5,1-f]-1,2,4-triazine, maleate 3,4-Dihydro-2,5-dimethyl-7-isobutylimidazo[5,1-f]-1,2,4-triazine (1.5 g) was heated under reflux in p-cymene (100 ml) with 10% palladium oxide on charcoal (2.85 g) for 4 hours. After cooling to room temperature the mixture was filtered through a diatomaceous earth and the catalyst washed with ethyl acetate. The filtrate and washings were extracted with 2 N hydrochloric acid (5×75 ml) and the extract washed with ethyl acetate (3×75 ml) and basified with solid sodium carbonate. The oily layer which separated was extracted into ethyl acetate (3×75 ml) and dried over magnesium sulphate. Removal of the solvent gave an orange oil (1.8 g). This material was absorbed on to silica gel (29 g) and eluted with ethyl acetate to give the product as a gum (1.0 g).

This material was taken up in anhydrous ether (20 ml) and added dropwise with stirring to a solution of maleic acid (0.7 g) in anhydrous ether (50 ml). The orange oil which separated slowly crystallised. Two recrystallisations from dry ether/ethyl acetate gave the monohydrate maleate salt (0.68 g) m.p. 100°–103°.

(ii) In a similar manner was prepared 2-benzyl-5-methyl-7-(2-methylpropyl)imidazo[5,1-f]-1,2,4-triazine, 0.2 g, m.p. 72.5°–74° (sublimed) from 2-benzyl-3,4-dihydro-5-methyl-7-(2-methylpropyl)imidazo[5,1-f]-1,2,4-triazine (0.95 g).

(iii) In a similar manner was prepared 5-methyl-7-(2-methylpropyl)-2-(1-methylethyl)imidazo[5,1-f]-1,2,4-triazine as an oil, 0.68 g [the hydrochloride salt had m.p. 144°–146° (dec.) from ethanol-ethyl acetate] from 3,4-dihydro-5-methyl-2-(1-methylethyl)-7-(2-methylpropyl)imidazo[5,1-f]-1,2,4-triazine (1.5 g).

EXAMPLE 10

3,4-Dihydro-2,5-dimethyl-7-propylimidazo[5,1-f]-1,2,4-triazine, hydrochloride (a) Ethyl-3-butyramido-2-oxo-butyrate Ethyl oxalyl chloride (409.5 g) was added dropwise with stirring to a solution of butyrylalanine (238.5 g), anhydrous pyridine (355.5 g) and 4-dimethylaminopyridine (6 g) in anhydrous tetrahydrofuran (1 liter) at a rate sufficient to initiate refluxing. The mixture was heated to maintain a gentle reflux for 1½ hours, then cooled, diluted with water (1 liter) and extracted with ethyl acetate (3×500 ml). The extract was washed with water (2×250 ml) and dried (anhydrous sodium sulphate). Removal of the solvent gave a mixture of enol esters as an orange syrup. This material contained polar impurities which were removed by column chromatography in two batches. The crude product was absorbed onto silica gel (2×700 g) and eluted with cyclohexane-ethyl acetate (3:1) to give the purified enol esters (293 g).

This material was dissolved in absolute ethanol (270 ml) and heated at reflux in the presence of sodium bicarbonate (66 g) for 2½ hours. The mixture was cooled and sodium bicarbonate removed by filtration. The filtrate was concentrated to give the α-ketoester as a golden-yellow syrup which was used directly in the next stage.

(b) 6-(1-Butyramido)ethyl-3-methyl-1,2,4-triazin-5(4H)-one

To an ice-cold solution of acetamidine hydrochloride (66.2 g) in absolute ethanol (600 ml) was slowly added a solution of hydrazine hydrate (35 g) in absolute ethanol (20 ml) over 20 minutes. After completion of the addition stirring was continued at room temperature for 10 minutes. A solution of ethyl 3-butyramido-2-oxo-butyrate (151 g) in absolute ethanol (100 ml) was then added and the mixture heated at 65°–70° with stirring for 20 hours. The precipitated ammonium chloride was removed by filtration and the filtrate concentrated in vacuo whereupon the triazinone separated. Ethyl acetate (ca. 300 ml) was added to aid the precipitation and the solid was collected. The filtrate was concentrated to give a second crop which was combined with the first and recrystallised from ethanol, 28.6 g. A further recrystallisation from ethanol afforded an analytical sample, m.p. 235°–237°.

(c) 2,5-Dimethyl-7-propylimidazo[5,1-f]-1,2,4-triazin-4(3H)-one 6-(1-Butyramido)ethyl-3-methyl-1,2,4-triazin-5(4H)-one (21.8 g) was added portionwise to polyphosphoric acid (220 g) at 160°. When all the solid had dissolved the mixture was heated for 1 hour with occasional stirring at 100°, then cooled and poured onto ice-water (ca. 1 liter). The pH was adjusted to ca. 7.5 by the addition of 8% sodium bicarbonate and the precipitated imidazotriazinone collected, dried and recrystallised from ethyl acetate. Extraction of the filtrate with ethyl acetate gave a second crop which was also recrystallised from ethyl acetate. Total yield: 16.2 g., m.p. 228°–231°.

The base (1.33 g) was dissolved in a minimum amount of absolute ethanol and ethereal hydrogen chloride added until the pH was 1–2. Dry ether was then added until precipitation ceased. The hydrochloride was collected and twice recrystallised from ethanol-ethyl acetate, m.p. 254°–258°, 0.79 g.

(d) 3,4-Dihydro-2,5-dimethyl-7-propylimidazo[5,1-f]-1,2,4-triazine, hydrochloride Lithium aluminium hydride (5.5 g) was added portionwise under nitrogen to a suspension of 2,5-dimethyl-7-propylimidazo[5,1-f]-1,2,4-triazin-4(3H)-one (16.6 g) in dry dimethoxyethane (450 ml). The addition was complete after 20 minutes. The mixture was heated at reflux for 2 hours, then cooled and treated sequentially with water (10 ml), 2 N sodium hydroxide (15 ml) and water (10 ml). The granular precipitate of aluminium salts was filtered off and the filtrate concentrated in vacuo. The partially crystalline residue was dissolved in ethyl acetate (200 ml) and the solution washed with water (25 ml) and dried (sodium sulphate). Removal of the solvent gave the dihydroimidazotriazine. Recrystallisation twice from ethyl acetate gave white crystals m.p. 143°–149° (dec.)., 11.4 g.

Part of the base (11.1 g) was dissolved in absolute ethanol (ca. 25 ml) and treated with ethereal hydrogen chloride until the solution was pH 2. Dry ether (ca. 100 ml) was added until precipitation ceased. The solid was collected and recrystallised from ethanol-ethyl acetate to give the hydrochloride salt, m.p. 251°–255°, 9.7 g.

EXAMPLE 11

(i) 3,4-Dihydro-7-(2-methylpropyl)-2,4,5-trimethylimidazo-[5,1-f]-1,2,4-triazine An ethereal solution (89 ml) of methyl magnesium iodide [prepared from methyl iodide (3.56 g) and magnesium turnings (0.6 g)] was added under nitrogen to a stirred solution of 2,5-dimethyl-7-(2-methylpropyl)imidazo[5,1-f]-1,2,4-triazine (2.5 g) in anhydrous ether (20 ml). The mixture was stirred at room temperature overnight and then aqueous ammonium chloride was added until all the solid dissolved. The ethereal layer was separated and the aqueous layer extracted further with ethyl acetate. The organic layers were combined and dried (anhydrous sodium sulphate). Removal of the solvent gave an orange solid. Recrystallisation from ethyl acetate-ether gave the adduct as a cream solid m.p. 164°–167°, 1.63 g.

The base (1.63 g) was dissolved in anhydrous ether (200 ml) and the solution cooled in an ice-bath and treated with ethereal hydrogen chloride, dropwise with stirring, until precipitation ceased. The hydrochloride was collected and recrystallised from ethanol-ethyl acetate to give material m.p. 198°–201.5°. A second recrystallisation gave m.p. 199°–206° (dec.), 1.47 g.

(ii) In a similar manner was prepared 3,4-dihydro-2,4,5-trimethyl-7-propylimidazo[5,1-f]-1,2,4-triazine, 1.31 g, m.p. 175°–179° (from ethyl acetate) (the hydrochloride salt had m.p. 224°–227° from ethanol-ethyl acetate) from 2,5-dimethyl-7-propylimidazo[5,1-f]-1,2,4-triazine (1.90 g).

EXAMPLE 12

2,5-Dimethyl-7-propylimidazo[5,1-f]-1,2,4-triazine

10% Palladium oxide on charcoal (2.2 g) was suspended in a solution of 3,4-dihydro-2,5-dimethyl-7-propylimidazo[5,1-f]-1,2,4-triazine (1.00 g) in p-cymene (100 ml) and the mixture was heated at reflux under nitrogen for 6 hours. The mixture was cooled and the catalyst removed by filtration through diatomaceous earth and washed thoroughly with hot ethanol. The filtrate and washings were combined and extracted with 2 N hydrochloric acid (2×75 ml). The extract was brought to pH 8 by the addition of aqueous sodium carbonate and extracted with ether (3×50 ml). The ethereal extract was dried (sodium sulphate) and concentrated and the residue absorbed onto silica gel. Elution with ethyl acetate afforded the imidazotriazine as a solid (0.56 g), which was sublimed at 50°–52°/0.02 mm Hg to give lemon yellow crystals m.p. 54°–56°.

Pharmaceutical Compositions

EXAMPLE 13

To prepare 10,000 capsules each containing 5 mg of active ingredient

Mix together 50 g powdered active ingredient with a sufficient quantity of microcrystalline cellulose BPC and fill into No. 3 hard gelatin capsules so that each capsule contains about 120 mg of the mixture.

Capsules may be similarly prepared each containing 10 mg active ingredient.

EXAMPLE 14

To prepare 5,000 tablets each containing 2 mg active ingredient

Mix together 10 g active ingredient, 585 g microcrystalline cellulose BPC, 5 g magnesium stearate and 5 g stearic acid. Compress the powders on a suitable tabletting press to produce tablets each 6 mm in diameter and weighing about 120 mg.

Tablets of other strengths may be prepared similarly.

Tablets may also be prepared by a wet granulation process as follows:

To prepare 5,000 tablets each containing 2 mg active ingredient, mix together 10 g active ingredient, 498 g lactose BP, 60 g Maize starch BP and 30 g Pregelatinised maize starch BP. Add sufficient cold water to produce a damp cohesive mass and pass the mass through a No. 14 mesh BSS sieve and dry the resulting granules in an oven or fluid bed dryer at 60° C. Pass the dried granules through a No. 22 BSS sieve and mix with 2 g magnesium stearate BP. Compress the granules on a suitable tabletting press to produce tablets 6 mm in diameter weighing about 120 mg.

Tablets of other strengths may be prepared similarly. The tablets may be film coated with suitable film forming materials such as methyl cellulose, hydroxypropylmethyl cellulose or mixtures of the materials using standard techniques.

The tablets may also be sugar coated by the standard sugar coating techniques.

EXAMPLE 15

To prepare 10 liters of flavoured syrup containing 2 mg active ingredient in each 5 ml Dissolve 5.5 kg sucrose BP in sufficient distilled water to produce 9 l. of syrup. Mix into the syrup 1 l. of glycerin and dissolve 4 g active ingredient, sufficient preservative, colour and flavour and filter through a suitable filter pad and distribute into bottles.

EXAMPLE 16

To prepare an injection containing 2 mg active ingredient in 5 ml

Dissolve 2 g active ingredient and 8.5 g sodium chloride in 950 ml water for injections. When solution is complete make up to 1 l. with more water for injection. Purge the solution with nitrogen and fill, under nitrogen, into suitable size ampoules (1 ml, 5 ml or 10 ml) seal and sterilise by heating in an autoclave.

EXAMPLE 17

To prepare suppositories each containing 2 mg active ingredient

Melt 4 kg of a suitable fatty suppository base and stir in 2 g active ingredient. Keeping the active ingredient suspended through the base by stirring, pour the mixture into suitable 4 g suppository moulds.

EXAMPLE 18

To prepare 1,000 pressurised aerosol cans each containing about 200 doses of 500 μg active ingredient per 85 mg shot Micronise the active ingredient so that the majority of the crystals are between 1 and 5 μm in longest dimension and none are greater than 10 μm. Disperse 120 g of the micronised active ingredient in 5.7 kg of a 0.21% w/w solution of Oleic Acid BP in Propellant 11 BPC. Make this suspension up to 20.4 kg with Propellant 12 BPC and fill into suitable sized aerosol cans by standard techniques. Seal the cans with a suitable metering valve capable of delivering 85 mg of suspension with each actuation.

EXAMPLE 19

To prepare 10,000 cartridges for inhalation each containing 1 mg active ingredient Micronise the active ingredient so that the majority of the crystals are between 1 μm and 5 μm in longest dimension and none are greater than 10 μm. Disperse 10 g of the micronised active ingredient in 240 g lactose BP. Fill about 25 mg of the powder into No. 3 hard gelatin capsules.

In all the above examples of pharmaceutical compositions, the active ingredient is a compound according to the invention.

We claim:

1. A compound which is a imidazo[5,1-f]-1,2,4-triazine or a derivative thereof of the formula (I):

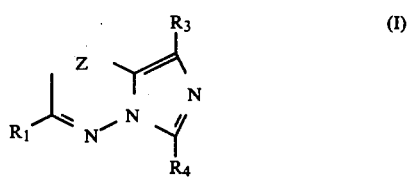

and physiologically acceptable salts thereof in which

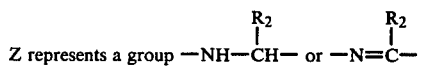

wherein $R_2$ represents a hydrogen atom or a straight or branched chain alkyl radical containing from 1 to 6 carbon atoms, or Z can additionally represent a group

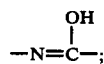

and $R_1$, $R_3$ and $R_4$, which may be the same or different, each represent a hydrogen atom; a cycloalkyl group, said cycloalkyl group containing from 3 to 7 carbon atoms; a phenyl group which may optionally be substituted by one or more hydroxy, alkoxy or halogen radicals, said alkoxy radical containing from 1 to 4 carbon atoms; or straight or branched alkyl or alkenyl group, said alkyl group containing from 1 to 6 carbon atoms, said alkenyl group containing 2 to 6 carbon atoms, which alkyl or alkenyl group may be substituted with a phenyl group, which phenyl group may optionally be substituted by one or more hydroxy, alkoxy or halogen radicals, said alkoxy radical containing from 1 to 4 carbon atoms.

2. A compound as claimed in claim 1 in which Z represents a group of the formula:

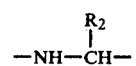

in which $R_1$ represents methyl, $R_2$ represents hydrogen or methyl, $R_3$ represents methyl, and $R_4$ represents n-propyl or isobutyl, except that $R_4$ does not represent isobutyl when $R_2$ represents hydrogen.

3. A compound as claimed in claim 1 in which:
$R_1$ is hydrogen, alkyl or phenyl or phenylalkyl;
$R_2$ is hydrogen or alkyl;
$R_3$ is alkyl or phenyl;
$R_4$ is alkyl or cycloalkyl.

4. A compound as claimed in claim 3 in which:
$R_1$ is hydrogen, methyl, ethyl or isopropyl, phenyl, benzyl or phenethyl;
$R_2$ is hydrogen or methyl;
$R_3$ is methyl or phenyl;
$R_4$ is methyl, propyl or isobutyl, or cyclopentyl.

5. A compound as claimed in claim 1 selected from 2,5-dimethyl-7-(2-methylpropyl)imidazo[5,1-f]-1,2,4-triazin-4(3H)-one and physiologically acceptable salts thereof.

6. A compound as claimed in claim 1 selected from 3,4-dihydro-2,5-dimethyl-7-propylimidazo[5,1-f]-1,2,4-triazine and physiologically acceptable salts thereof.

7. A compound as claimed in claim 1 selected from 3,4-dihydro-7-(2-methylpropyl)-2,4,5-trimethylimidazo[5,1-f]-1,2,4-triazine and physiologically acceptable salts thereof.

8. A compound as claimed in claim 1 selected from 2-(1-methylethyl)-5-methyl-7-(2-methylpropyl)imidazo[5,1-f]-1,2,4-triazin-4(3H)-one, and physiologically acceptable salts thereof.

9. A pharmaceutical composition comprising at least one compound as claimed in claim 1 in association with a physiologically acceptable carrier.

10. A composition as claimed in claim 9 including supplementary medicinal agents.

11. A composition as claimed in claim 9 in the form of solid or liquid preparations for oral use, as suppositories or injections or forms suitable for inhalation.

12. A composition as claimed in claim 11 in the form of a powder which may be inhaled.

13. A composition as claimed in claim 9 in dosage unit form.

14. A method for the treatment of a patient suffering from a condition involving constriction of the bronchial muscle which comprises administering an effective amount of a compound as claimed in claim 1.

* * * * *